(12) United States Patent
Gerber

(10) Patent No.: US 11,324,859 B2
(45) Date of Patent: May 10, 2022

(54) CARRIER COMPOSITION FOR BONE SUBSTITUTE MATERIALS

(71) Applicant: ARTOSS GMBH, Rostock (DE)

(72) Inventor: Thomas Gerber, Papendorf (DE)

(73) Assignee: ARTOSS GMBH, Rostock (DE)

( * ) Notice: Subject to any disclaimer, the term of this patent is extended or adjusted under 35 U.S.C. 154(b) by 247 days.

(21) Appl. No.: 16/498,787

(22) PCT Filed: Mar. 29, 2018

(86) PCT No.: PCT/EP2018/058132
§ 371 (c)(1),
(2) Date: Sep. 27, 2019

(87) PCT Pub. No.: WO2018/178266
PCT Pub. Date: Oct. 4, 2018

(65) Prior Publication Data
US 2021/0093752 A1    Apr. 1, 2021

(30) Foreign Application Priority Data

Mar. 29, 2017 (EP) .................................... 17163687

(51) Int. Cl.
| A61L 27/52 | (2006.01) |
| A61L 27/18 | (2006.01) |
| A61L 27/38 | (2006.01) |
| A61L 27/44 | (2006.01) |
| C08L 71/02 | (2006.01) |

(52) U.S. Cl.
CPC ............... *A61L 27/52* (2013.01); *A61L 27/18* (2013.01); *A61L 27/3821* (2013.01); *A61L 27/446* (2013.01); *C08L 71/02* (2013.01); *A61L 2400/12* (2013.01); *A61L 2430/02* (2013.01)

(58) Field of Classification Search
CPC combination set(s) only.
See application file for complete search history.

(56) References Cited

U.S. PATENT DOCUMENTS

| 2013/0045920 A1* | 2/2013 | Shimko ............... A61L 24/0084 |
| | | 514/8.8 |
| 2014/0105884 A1* | 4/2014 | Konorty .................... A61K 9/06 |
| | | 424/94.67 |
| 2016/0051725 A1* | 2/2016 | Ryu ........................ A61L 27/54 |
| | | 424/489 |
| 2021/0093752 A1* | 4/2021 | Gerber ..................... A61L 27/46 |

FOREIGN PATENT DOCUMENTS

| WO | 0160409 | 8/2001 | |
| WO | 2004071452 | 8/2004 | |
| WO | 2007025698 | 3/2007 | |
| WO | 2011137231 | 11/2011 | |
| WO | 2012117260 | 9/2012 | |
| WO | 2014095915 | 6/2014 | |
| WO | 2014099967 | 6/2014 | |
| WO | 2014157985 | 10/2014 | |
| WO | 2016037249 | 3/2016 | |
| WO | WO-2016037249 A1 * | 3/2016 | ........... A61K 31/519 |

OTHER PUBLICATIONS

Machine translation of WO-2016037249-A1 (Year: 2016).*
International Search Report and Written Opinion in corresponding PCT/EP2018/058132, dated Jun. 6, 2018.
XP002773868—Database WPI, 0, Derwent World Patents Index, vol. 2016, No. 23, Database accession No. 2016-166488, & WO2016037249 A1 20160317 (Unicamp Univ Estadual Campinas) [X] 1-4,6-8 abstract paragraphs [0035], [0 41], [0 42], [0 45], [0 58]—[0070] (2016).
Munoz et al, "Localized inhibition of P2X7R at the spinal cord injury site improves neurogenic bladder dysfunction by decreasing urothelial P2X3R expression in rats", Life Sciences., vol. 171, pp. 60-67 (Dec. 27, 2016).
Kienast B et al., "Nanostrukturiertes synthetisches Knochenmaterial zur Behandlung von Knochendefekten", Trauma und Berufskrankheit, Springer-Verlag, Berlin/Heidelberg, vol. 18, No. 4, pp. 308-318 (Oct. 21, 2016).
Anonymous, NanoBone SBX Putty—"Summary for ARTG Entry: 292263 Global Orthopaedic Technology Pty Ltd—NanoBone SBX Putty—Bone matrix implant, synthetic," The Therapeutic Goods Administration (TGA)—Australian Government Department of Health, URL: https://www.ebs.tga.gov.au/servlet/xmlmillr6?dbid=ebs/PublicHTML/pdfStore.nsf&docid=292263&agid=(PrintDetailsPublic)&actionid=1, XP055406921 [XP] 1-15 (Jul. 31, 2017).
Mortensen, et al.,Macromolecules, (1993), vol. 26. No. 4, pp. 805-812.
Extended European Search Report in corresponding European Patent Application No. 1716387.1.

* cited by examiner

Primary Examiner — Peter A Salamon
(74) Attorney, Agent, or Firm — Hovey Williams LLP

(57) ABSTRACT

The present invention relates to a carrier composition for particulate and granular bone substitute materials which is a hydrogel comprising a mixture of ethylene oxide (EO)-propylene oxide (PO) block copolymers and silica nanoparticles embedded therein. The present invention further relates to a bone substitute material containing osteoconductive and/or osteoinductive particles or granules in addition to the novel carrier composition. Processes for producing the novel carrier composition and the novel bone substitute material are likewise provided in the context of the invention.

19 Claims, 8 Drawing Sheets

CARRIER COMPOSITION FOR BONE SUBSTITUTE MATERIALS

CROSS-REFERENCE TO RELATED APPLICATIONS

This application is the U.S. National Stage of International Patent Application No. PCT/EP2018/058132, filed Mar. 29, 2018, which is hereby incorporated by reference in its entirety, and which claims priority to European Patent Application No. 17163687.1, filed Mar. 29, 2017.

FIELD OF INVENTION

The present invention relates to a carrier composition for particulate and granular bone substitute materials, which is a hydrogel comprising a mixture of ethylene oxide (EO)-propylene oxide (PO) block copolymers and silica nanoparticles embedded therein. The present invention also relates to a bone substitute material which, in addition to the novel carrier composition, contains osteoconductive and/or osteoinductive particles or granules. Methods for preparing the novel carrier composition and the novel bone substitute material are also provided within the framework of the invention.

BACKGROUND OF THE INVENTION

Bone replacement materials have a functionality that is determined by their structure and composition. Bone replacement materials unfold their effect through interaction of the material surface with proteins, e.g. those that control bone metabolism, and surface structures that promote cell adhesion. Bone replacement materials known in the prior art are usually ceramics or bioglasses, which are usually used in granular form. Before application, these granules are mixed with the patient's blood so that the surface of the granules is coated with autologous proteins. Coagulation of the blood produces a paste-like mass which can be introduced, for example, into bone defects.

However, the production of these bone substitute materials is associated with considerable disadvantages. The necessity of mixing the bone substitute material with blood and waiting for coagulation regularly complicates the course of an operation. For this reason, it has been attempted in the prior art to develop a carrier material for bone substitute materials that makes mixing with blood superfluous. Here it is important to be able to adapt the rheological properties to the concrete applications. On the one hand, a carrier material for bone substitute granules should be dimensionally stable and hydrostable if possible, and it should also have a sufficient adhesive effect after insertion into a strongly bleeding defect. On the other hand, the carrier material should be present in a dosage form that allows administration by means of a cannula.

WO 2004/071452 A2 describes poloxamers, such as Poloxamer 407, for medical and surgical applications. WO 2012/117260 A2 discloses a synthetic bone substitute material in which ceramic particles are embedded in a hydrogel carrier. The hydrogel is preferably a hydrogel based on Poloxamer 407. WO 2014/099967 A2 also describes a bone substitute material that contains ceramic components in a hydrogel that is based on Poloxamer 407. US 2016/0051725 discloses a poloxamer-based hydrogel containing calcium phosphate particles and describes how the viscoelastic and rheological properties of hydrogels can be improved by additives. US 2013/0045920 describes a bone replacement material comprising a ceramic material, a poloxamer 407 hydrogel and polysaccharide additives. WO 2014/095915 A2 describes a thermo-reversible hydrogel on poloxamer basis, which is supposed to allow a versatile application in the medical field. Gel formation in these hydrogels takes place via the temperature-dependent formation of micelles by the block polymers. However, the hydrogels described in the state of art have the disadvantage that their viscosity is too low to guarantee a sufficiently high formability and stickiness of the hydrogel.

In order to ensure smooth application of the bone substitute materials, a ready-to-use carrier material would be required which is easy to shape and sufficiently sticky to be fixed in a defect. Furthermore, the material should be hydrostable, i.e. it should not be flushed away even in the case of heavily bleeding wounds. Ideally, it should be possible to insert it directly into the defect from an appropriate applicator.

The objective of the present application therefore is to develop a carrier material which meets the above requirements.

DESCRIPTION OF THE INVENTION

The present invention provides a novel composition that can be used as a carrier for particulate and granular bone substitute materials. The carrier composition is a hydrogel comprising:

(a) an ethylene oxide (EO)-propylene oxide (PO) block copolymer or a mixture of ethylene oxide (EO)-propylene oxide (PO) block copolymers; and
(b) silica nanoparticles.

In the hydrogels according to the invention, gel formation takes place by cross-linking of the ethylene oxide (EO)-propylene oxide (PO) block copolymers with the silica nanoparticles. The rheological properties can be modified and adapted to different applications by specific modification of the hydrogel components. In contrast to conventional hydrogels based on block copolymers, the gel formation in the hydrogels according to the invention does not take place through micelle formation, but through direct interactions between the silica nanoparticles and the block copolymers. The hydrogels of the present invention therefore contain no or only a small proportion of block copolymers in the form of micelles. Preferably, the proportion of block copolymers in the form of micelles is below 2%, and more preferably below 1%. In a particularly preferred embodiment, the hydrogels of the present invention do not comprise micelles. Since the hydrogels of the invention are not based on the formation of micelles, they are not thermo-sensitive, i.e. the sol-gel transition of these hydrogels does not depend on the temperature. The invention hydrogels are thermo-stable and do not become liquid even at low temperatures.

It was found in the framework of the present invention that the new carrier composition does not negatively influence the biological processes of bone healing. No negative interaction of the carrier composition with the surface of the bone substitute material has been demonstrated, e.g. by preventing the coating of this surface with autologous proteins or by clogging of nanopores. In addition, the new carrier composition has viscoelastic and rheological properties that ensure rapid resorption. The new carrier composition therefore makes a mixture of the known granules with blood superfluous. Instead, the bone substitute materials in granular form are mixed directly with the new carrier composition and inserted into the defect. This leads to a significant simplification in clinical practice.

The carrier composition is a hydrogel based on one or more block copolymers of ethylene oxide and propylene oxide. The block copolymers are preferably poloxamers. Poloxamers are low-foaming, non-ionic surfactants which are widely used in dispersing and emulsifying in the chemical-technical industry. The polyethylene oxide part of the polymer is water-soluble, but the polypropylene oxide part is not, so that the amphiphilic properties result. Depending on the degree of ethoxylation, they are liquid (L), pasty (P), solid (F) or powdery. Poloxamers have good biocompatibility, are not metabolizable under physiological conditions, hardly toxic or corrosive, and are easily eliminated from the body.

Poloxamers were developed by BASF in the 1950s and have since been marketed under the brand name Pluronic®. Due to their amphiphilic structure, poloxamers are able to form so-called lyotropic association colloids in aqueous multi-component mixtures. In this process, a so-called thermo-gelling behaviour occurs. This means that poloxamer solutions can change their colloidal structure depending on the temperature and thereby form reversible gel structures. If poloxamers are brought into contact with water, hydration takes place with the formation of hydrogen bonds. When the temperature increases, the binding forces of these hydrogen bonds are reduced and thus dehydration occurs, whereby the more hydrophobic polypropylene oxide parts are predominantly affected. This hydrophobization causes an association of the lipophilic propylene oxide units to micelles and, with a further increase in temperature and sufficient poloxamer concentration, to the formation of a gel scaffold of densely packed micelles. These surfactant gels are optically isotropic and therefore crystal clear.

A preferred poloxamer for the production of the carrier composition of the present invention is the Poloxamer 407, which is also marketed under the name Kolliphor P 407. Poloxamer 407 is used in particular for pharmaceutical preparations and medical devices and has the following structural formula:

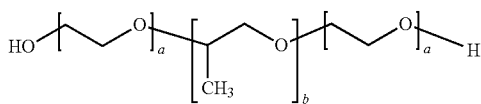

wherein the block lengths are about a=101 and b=56. While the use of Poloxamer 407 as the starting substance for the production of the carrier compositions of the present invention is particularly preferred, other poloxamers, such as Poloxamer 188, can also be used.

Aqueous solutions of Poloxamer 407 show a so-called thermogelling at concentrations of 20-30%. This gelling process is completely reversible when the temperature is subsequently lowered (Mortensen & Pedersen (1993), Macromolecules 26(4), pp. 805-812). The thermogelling point (TGP) of a composition, i.e. the temperature at which such a sol-gel conversion takes place, can be easily determined using oscillation rheology.

The proportion of ethylene oxide (EO)-propylene oxide (PO) block copolymers in the carrier composition is preferably between about 10% and about 40% (w/w), and preferably between about 20% and about 37% (w/w). For example, the proportion of ethylene oxide (EO)-propylene oxide (PO) block copolymers in the carrier composition can be 10%, 15%, 20%, 25%, 30%, 35%, or 40%. The proportion of water in the carrier compositions is usually between about 60% and about 90% (w/w). The proportion of water in the carrier compositions can be about 60%, 65%, 70%, 75%, 80%, 85%, or 90% (w/w).

In a preferred embodiment, the ethylene oxide (EO)-propylene oxide (PO) block copolymers in the carrier composition have a molecular weight distribution between about 1,000 g/mol and 70,000 g/mol. In a particularly preferred embodiment, at least 30% (w/w), preferably 40% (w/w), of the ethylene oxide (EO)-propylene oxide (PO) block copolymers in the carrier composition consist of a poloxamer, preferably Poloxamer 407, which has an average molecular weight in the range from 9,800 to 14,600 g/mol.

In the course of the invention it was surprisingly found that the viscosity of a hydrogel based on a poloxamer, such as Poloxamer 407, can be considerably increased by the addition of silica nanoparticles. As shown in the following examples, the addition of nanoparticles increases the viscosity of poloxamer-based hydrogels by a factor of 10 and thus allows the use of the hydrogels as shapeable pasty carrier materials. The proportion of silica nanoparticles in the carrier composition of the invention is preferably between about 2% and about 12% (w/w), preferably in the range between about 3.5% and about 5% (w/w). It is particularly preferred that the proportion of silica nanoparticles in the carrier composition is about 2%, 3%, 4%, 5%, 6%, 7%, 8%, 9%, 10%, 11% or 12% (w/w).

Silica nanoparticles are defined as particles with a size of less than 1 µm. The silica nanoparticles preferably have a size between about 0.5 nm and about 50 nm, more preferably between about 0.5 nm and about 10 nm, and even more preferably between about 0.5 nm and about 1.5 nm. Silica nanoparticles should preferably not form fractal clusters. If the silica nanoparticles form fractal aggregation clusters, these clusters preferably have a size of less than about 500 nm, more preferably less than about 200 nm, and even more preferably less than about 100 nm. Preferably, aggregation clusters containing less than 15 nanoparticles are used, e.g. less than 10 or less than 5.

Since a water-based gel is the basis for the carrier composition of to the present invention, it makes sense to produce the silica nanoparticles from a sodium water glass solution. When using a typical sodium water glass solution as a starting substrate with a $SiO_2$ concentration of about 27% and a $Na_2O$ concentration of about 8%, sol particles of about 0.5 nm are formed. The sodium ions can be replaced by hydrogen using an ion exchanger, resulting in a pure silica sol. Since the particle surface of the silica nanoparticles interacts with the polymer molecules, non-aggregated sol particles should preferably be used for the carrier composition. After the ion exchange, the pH value of the sol is usually 2 to 3. At this pH value, aggregation of the sol particles to clusters takes place very slowly and can be further slowed down by cooling the sol. A typical $SiO_2$ concentration, at which further processing can be carried out without any problems, is 6%. Cooling and fast processing allow $SiO_2$ concentrations of up to 12%. Stabilization of the sol is also possible by changing the pH to a value greater than 7. Since an implantable biomaterial with a pH value of about 7.5 is ultimately to be produced, a pH above 8 is not preferred. After the sol has been prepared, it can be mixed immediately with a solution of the polymer. Alternatively, the polymer can also be stirred directly into the sol.

The carrier compositions of the present invention are sufficiently viscous to ensure good formability and high stickiness. The carrier compositions provided herein preferably have a viscosity in the range of more than 900 Pas, preferably more than 1,000 Pas, when measuring the viscosity as a function of the shear rate using the StrainSweep Test, oscillation rheometer ARES—T.A. Instruments, shear rate 50 1/s.

Particularly preferred carrier compositions have the following composition:
- Proportion of EO-PO block copolymers between about 10% and about 40% (w/w), proportion of silica nanoparticles between about 2% and about 12% (w/w);
- Proportion of EO-PO block copolymers between about 15% and about 37% (w/w), proportion of silica nanoparticles between about 3% and about 10% (w/w);
- Proportion of EO-PO block copolymers between about 20% and about 30% (w/w), proportion of silica nanoparticles between about 3% and about 6% (w/w);
- Proportion of EO-PO block copolymers between about 20% and about 25% (w/w), proportion of silica nanoparticles between about 3% and about 5% (w/w).

In another aspect, the invention relates to a process for the production of a carrier composition for particulate and granular bone substitute materials, comprising mixing:
(a) an aqueous solution of an ethylene oxide (EO) propylene oxide (PO) block copolymer or a mixture of ethylene oxide (EO)-propylene oxide (PO) block copolymers, and
(b) silica nanoparticles
with each other and formulating them into a hydrogel. Both components are preferably available as aqueous solutions at the time of mixing.

The carrier compositions described above can be used for the production of bone substitute materials by combining conventional osteoconductive or osteoinductive particles or granules with the carrier compositions. In a further aspect, the invention thus provides a bone substitute material comprising at least the following components:
(a) a carrier composition as described above; and
(b) osteoconductive and/or osteoinductive particles or an osteoconductive and/or osteoinductive granules.

In principle, all known osteoconductive and/or osteoinductive particles and granules can be used with the novel carrier compositions. The term "osteoinductive" is used to describe particles and granules that are capable of stimulating new bone formation after implantation, wherein ectopic bone formation also occurs (bone formation in the muscle or in fat tissue). In contrast, "osteoconductive" refers to particles and granules that are able to serve as a scaffold structure for new bone formation after implantation.

The novel carrier compositions are suitable for use with all known alloplastic, xenogenic and allogenic materials. The carrier compositions can be used in particular with synthetic ceramic granules, such as tricalcium phosphate (TCP) ceramics or hydroxyapatite (HA) ceramics. In the production of synthetic ceramics, powdery starting materials are subjected to a sintering process at high pressure and temperatures of 1,000 to 1,500° C. The preferred calcium-phosphorus ratio of the ceramics is between 1.5 and 1.7. The ceramics are preferably porous so that sufficient osteointegration is ensured by penetrating the ceramic with new bone tissue. Pores with a size of 150-500 μm are optimal for bone ingrowth and resorption. Smaller pore sizes usually only lead to the growth of new bone tissue.

In addition to ceramics, bioglasses can also be used. Bioglasses, such as Biogran®, are amorphous materials containing acidic oxides, such as phosphorus pentoxide, silicon dioxide or aluminium oxide, and basic oxides such as calcium oxide, magnesium oxide and zinc oxide. During production, the oxides are mixed and melted in a process lasting several hours at high temperatures of about 1,500° C. The resulting bioglass represents a three-dimensional phosphorus oxide-silicon oxide network to which the corresponding metal ions of the basic oxides attach. Bioglasses are available in compact form and also in porous form. The bioactivity of the surface allows bone tissue to grow.

In addition to the above-mentioned granules, which usually have a size in the range of 0.1 to 5 mm, particles such as microparticles can also be used. Preferably, these osteoconductive or osteoinductive particles have a size between about 5 μm and 100 μm, more preferably between about 20 μm and 40 μm.

The osteoconductive or osteoinductive particles may, for example, be hollow spheres with an opening (donut shape). These can have a diameter in the range of 40 μm. FIG. 10 shows examples of osteoconductive or osteoinductive particles in the form of hollow spheres. As explained below, such particles should be coated with a silica hydrogel before embedding in the poloxamer hydrogel to avoid air inclusions. The resulting bone substitute material can be produced in a form which can be injected through conventional cannulae. Microparticles, such as hollow spheres, can also be used in clusters. Such clusters preferably have a size between about 100 μm and 3,000 μm. The clusters should also be coated with a silica hydrogel before embedding them into the poloxamer-silica hydrogel, as shown schematically in FIG. 11.

In a particularly preferred embodiment, the osteoconductive and/or osteoinductive particles or the osteoconductive and/or osteoinductive granules consist of hydroxyapatite crystallites with a morphology of the biological hydroxyapatite of the bone, which are embedded in a matrix of silica-xerogel. These particles or granules can also be coated with a silica hydrogel to avoid air inclusions before embedding them in the poloxamer hydrogel.

Preferably, the osteoconductive or osteoinductive particles or granules are porous materials. Porous or highly porous bone substitute materials with a high specific surface area have decisive advantages in supporting bone regeneration, as autologous proteins interact with the surface of the material.

If the carrier compositions described herein are used in combination with porous or highly porous particles or granules, these are preferably treated accordingly before embedding them into the poloxamer-silica hydrogel in order to avoid air inclusions. Due to the high viscosity, the poloxamer-silica hydrogel cannot penetrate into the pores of the particles or granules in some cases. The resulting air inclusions can impair or even completely prevent the functionality of the biomaterial. Furthermore, the polymer chains from the poloxamer-silica hydrogel could cover the surface of the bone substitute material and thus prevent interaction with autologous proteins. Thus, the pores of the particles or granules can be treated with a pure silica gel so that all pores are filled and a silica hydrogel layer surrounds the particles or granules. The silica gel used for surrounding can have a silica concentration between about 3% and about 10%. The coated particles or the coated granules can then be embedded in the poloxamer-silica hydrogel. A corresponding procedure is described in example 2. Thus, in a preferred embodiment the invention relates to a bone substitute material containing osteoconductive and/or osteoinductive particles, such as microparticles, coated with a silica gel.

Finally, the present invention also provides a method for the production of a bone substitute material, said method comprising:
(a) providing a carrier composition as described above;
(b) optionally treating the carrier composition with gamma radiation; and (c) mixing the carrier composition with osteoconductive and/or osteoinductive particles or osteoconductive and/or osteoinductive granules.

When preparing a bone substitute material based on the novel carrier composition, a carrier composition as described above is first provided. This carrier composition can be treated with gamma radiation to sterilize the composition before mixing it with the corresponding osteoconductive or osteoinductive particles or granules. The intensity of the radiation will usually be between 10 and 50 kGray, preferably between 17.5 and 30 kGray. The carrier composition is then mixed with osteoconductive and/or osteoinductive particles or osteoconductive and/or osteoinductive granules.

Mixing may be effected in the ratio (w/w) of carrier composition to particles or granules of about 5:1, 4:1, 3:1, 2:1, 1:1, 1:2, 1:3, 1:4 or 1:5. A ratio of about 1:1 is preferred. The bone substitute material so produced can then be stored until further use. For example, the bone substitute material can be filled into an applicator which facilitates the administration of the material to a defect site.

In a preferred embodiment, the osteoconductive and/or osteoinductive particles or the osteoconductive and/or osteoinductive granules are treated prior to mixing with the carrier composition in order to avoid air inclusions. It is particularly preferred according to the invention that the osteoconductive and/or osteoinductive particles or the osteoconductive and/or osteoinductive granules are coated with a silica hydrogel before mixing with the carrier composition, as described above.

In another aspect, the invention relates to the use of a carrier composition as described above for producing a bone substitute material. Thus, the invention relates to the use of a hydrogel comprising the following:
(a) an ethylene oxide (EO)-propylene oxide (PO) block copolymer or a mixture of ethylene oxide (EO)-propylene oxide (PO) block copolymers; and
(b) silica nanoparticles,
for the manufacturing of a bone substitute material.

Manufacturing includes mixing with osteoconductive and/or osteoinductive particles or osteoconductive and/or osteoinductive granules as defined above.

In another aspect, the invention relates to a bone substitute material as described above comprising at least the following components:
(a) a carrier composition as described above; and
(b) osteoconductive and/or osteoinductive particles or osteoconductive and/or osteoinductive granules as described above,
for use in a method of treating bone defects. Bone defects can be fractures, cancellous bone defects or cavities.

EXAMPLES

The following examples illustrate the effectiveness as well as the advantages of the carrier composition according to the invention and the bone substitute material formulated from it.

Example 1: Production of Hydrogels with and without $SiO_2$

Figure 1:
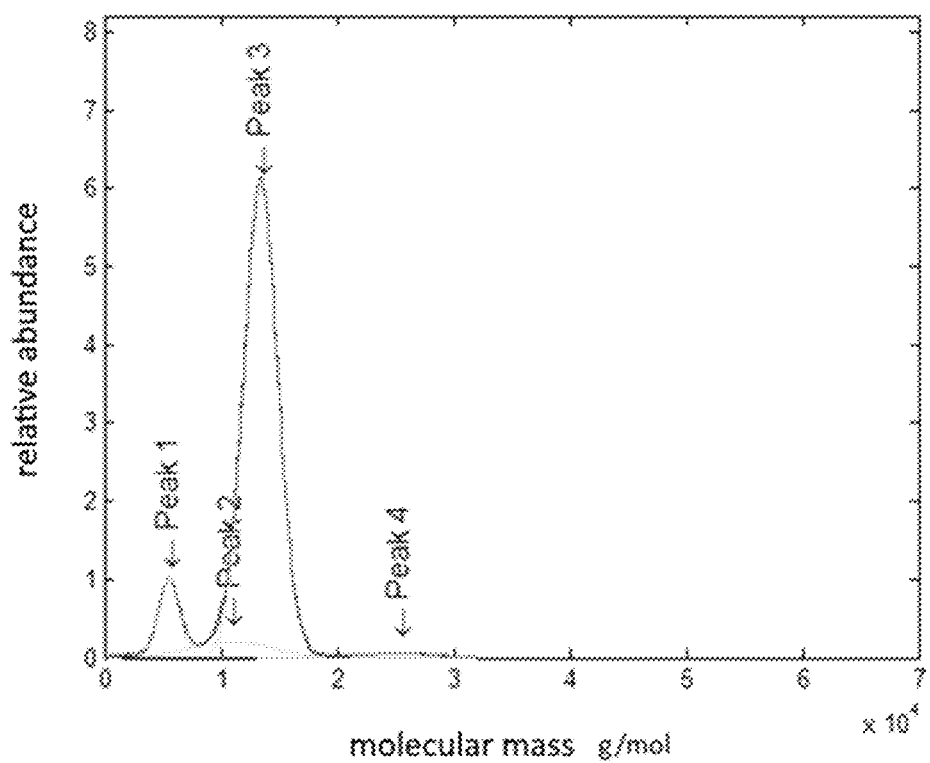
FIG. 1 shows the molecular mass distribution of a $SiO_2$-containing hydrogel based on Kolliphor P 407.

For comparison purposes, $SiO_2$-free and SiO2-containing hydrogels were produced on the basis of Kolliphor P 407. For the production of the $SiO_2$-free hydrogels, 23.5 g Kolliphor P 407 from BASF were mixed with 76.5 g water. For the hydrogels containing $SiO_2$, a sol was prepared by ion exchange with a $SiO_2$ concentration of 4% and 6%, respectively. Concentrated sodium water glass solution from Merk (specification: $Na_2O$: 7.5-8.5%; $SiO_2$: 25.5-28.5%) was used and diluted with ultrapure water. A Lewatit MonoPlus SP 112Na+ column was used as an ion exchanger. The soles had a pH value of 2.7 and were cooled down to 5° C. In each 76.5 g of the sol 23.5 g of Kolliphor P 407 were stirred in. The resulting hydrogels contain polymers with the molecular mass distribution shown in FIG. 1 (molecular mass distribution A). The molecular mass distribution can be determined by chromatography. The analysis led to the following peaks:

Peak 1: Position: 5,550 g/mol, proportion: 17.8%
Peak 2: Position: 11,000 g/mol, proportion: 8.2%
Peak 3: Position: 13,470 g/mol, proportion: 73.1%
Peak 4: Position: 25,500 g/mol, proportion: 0.8%

The peaks at 5,550 g/mol and 11,000 g/mol represent fragments of Kolliphor 407. The peak at 25,500 g/mol results from the cross-linking of two chains.

Some of the prepared samples were treated with gamma radiation (17.5 to 30 kGray, radiation source: cobalt 60, maximum activity 111 PBq). The gamma radiation leads to a cross-linking of the polymer chains. At the same time, chains are also broken. The result is a polymer with a broad molecular mass distribution.

Figure 2:
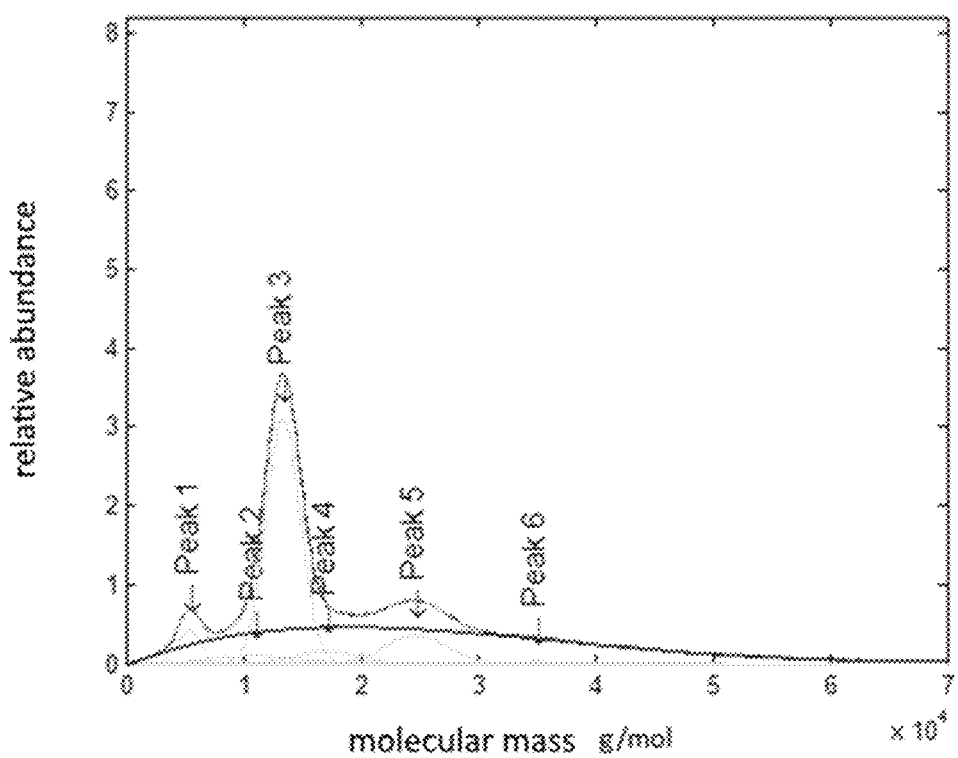
FIG. 2 shows the molecular mass distribution of a $SiO_2$-containing hydrogel based on Kolliphor P 407 after gamma irradiation.

These hydrogels contain polymers with the molecular mass distribution shown in FIG. 2 (molecular mass distribution B). The analysis led to the following peaks:
Peak 1: Position: 5,400 g/mol, proportion: 8.1%
Peak 2: Position: 11,000 g/mol, proportion: 4.0%
Peak 3: Position: 13,400 g/mol, proportion: 37.0%
Peak 4: Position: 17,000 g/mol, proportion: 2.7%
Peak 5: Position: 25,500 g/mol, proportion: 4.2%
Peak 6: Position: 35,000 g/mol, proportion: 0.2%

After irradiation, the proportion of the continuous mass distribution was 43.8%. The original Kolliphor 407 only has a proportion of 37%. Molecules with a continuous size distribution of up to approx. 70,000 g/mol have the largest proportion of 43.8%.

Figure 3:
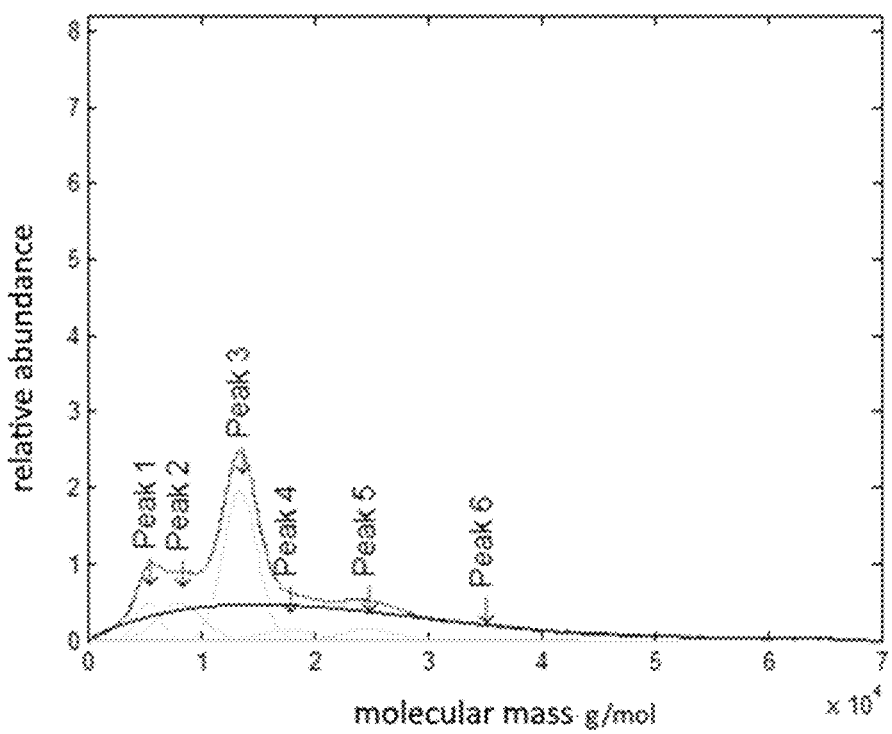
FIG. 3 shows the molecular mass distribution of a $SiO_2$-containing hydrogel based on Kolliphor P 407 after storage of the hydrogel at 60° C. for 55 days.

Another part of the prepared samples was stored at elevated temperature for a longer period of time. After storage for 55 days at 60° C., the hydrogels contained polymers with the molecular mass distribution shown in FIG. 3 (molecular mass distribution C). The analysis led to the following peaks:
Peak 1: Position: 5,350 g/mol, proportion: 10.6%
Peak 2: Position: 8,200 g/mol, proportion: 13.7%
Peak 3: Position: 13,470 g/mol, proportion: 23.6%
Peak 4: Position: 17,700 g/mol, proportion: 1.9733%
Peak 5: Position: 24,700 g/mol, proportion: 1.5018%.
Peak 6: Position: 35,000 g/mol, proportion: 0.0%

It can be seen that also in this case molecules with a size distribution ranging from about 1,000 g/mol to about 70,000 g/mol show the largest proportion of 48.7%.

Figure 4A:
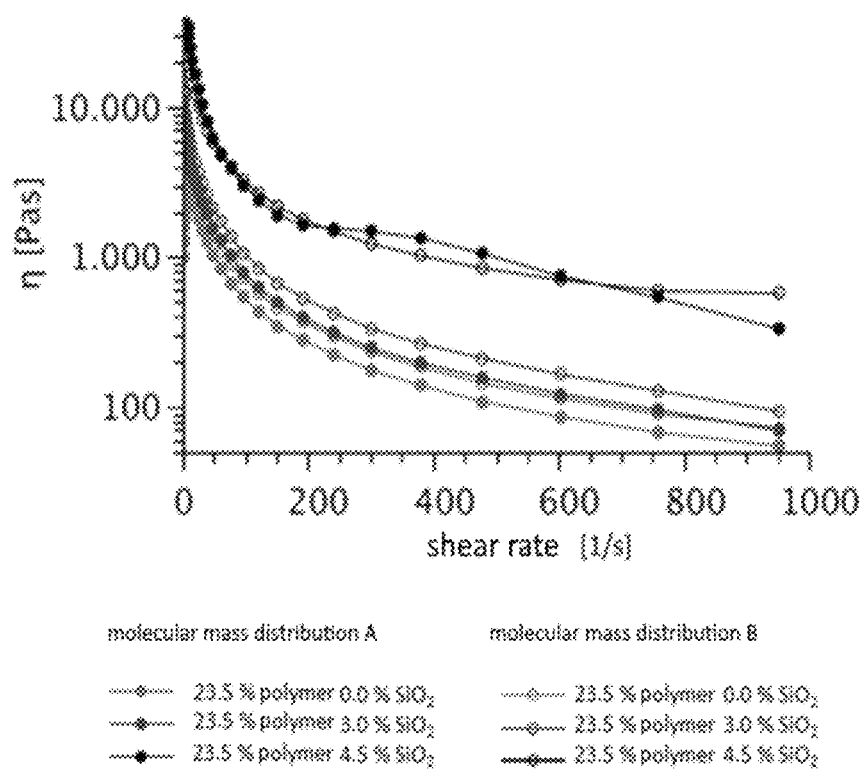
FIG. 4a shows the results of the viscosity measurement as a function of the shear rate.
Figure 5:
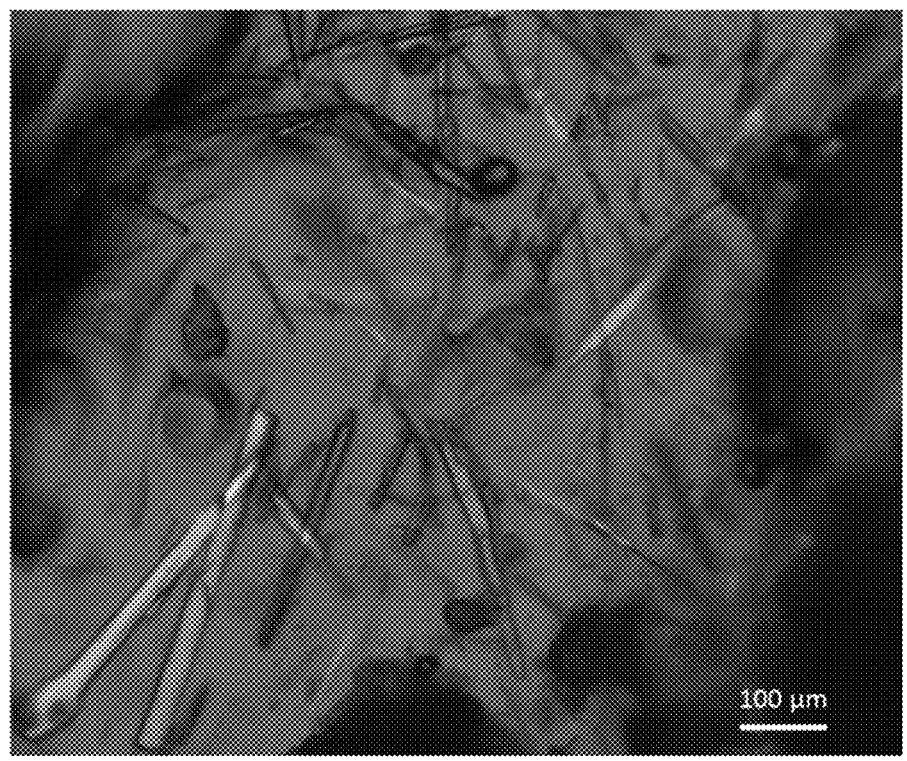
FIG. 5 shows the formation of lamellar structures under the polarization microscope.

For all samples the viscosity was measured as a function of the shear rate (StrainSweep Test, oscillation rheometer ARES—T.A. Instruments). The results are shown in FIG. 4a. It can be seen that the viscosity of both the $SiO_2$-free hydrogels and the $SiO_2$-containing hydrogels increases with the broadening of the molecular mass distribution. The samples with the molecular mass distribution A are not optically active, they show no contrast in the polarization microscope. This means that the polymers form micelles. The samples with the molecular mass distribution B, on the other hand, are optically active. They show a contrast in the polarizing microscope. This shows that the samples also contain so-called lamellar structures in addition to micelles. At high concentrations, some surfactants form lamellar structures in which the water is located in the polar intermediate layers of the associations. This optical anisotropy changes the plane of oscillation of the linearly polarized light so that characteristic light-dark appearances can be seen under the polarization microscope. FIG. 5 shows a typical example that documents the emergence of lamellar structures. Furthermore, FIG. 4a shows that the viscosity strongly increases with increasing $SiO_2$ content in the hydrogel. At a shear rate of 50 1/s, the viscosity increases 10-fold with the addition of 4.5% $SiO_2$. This is of decisive importance for the applicability of the gels as carriers for bone substitute materials.

Figure 4B:
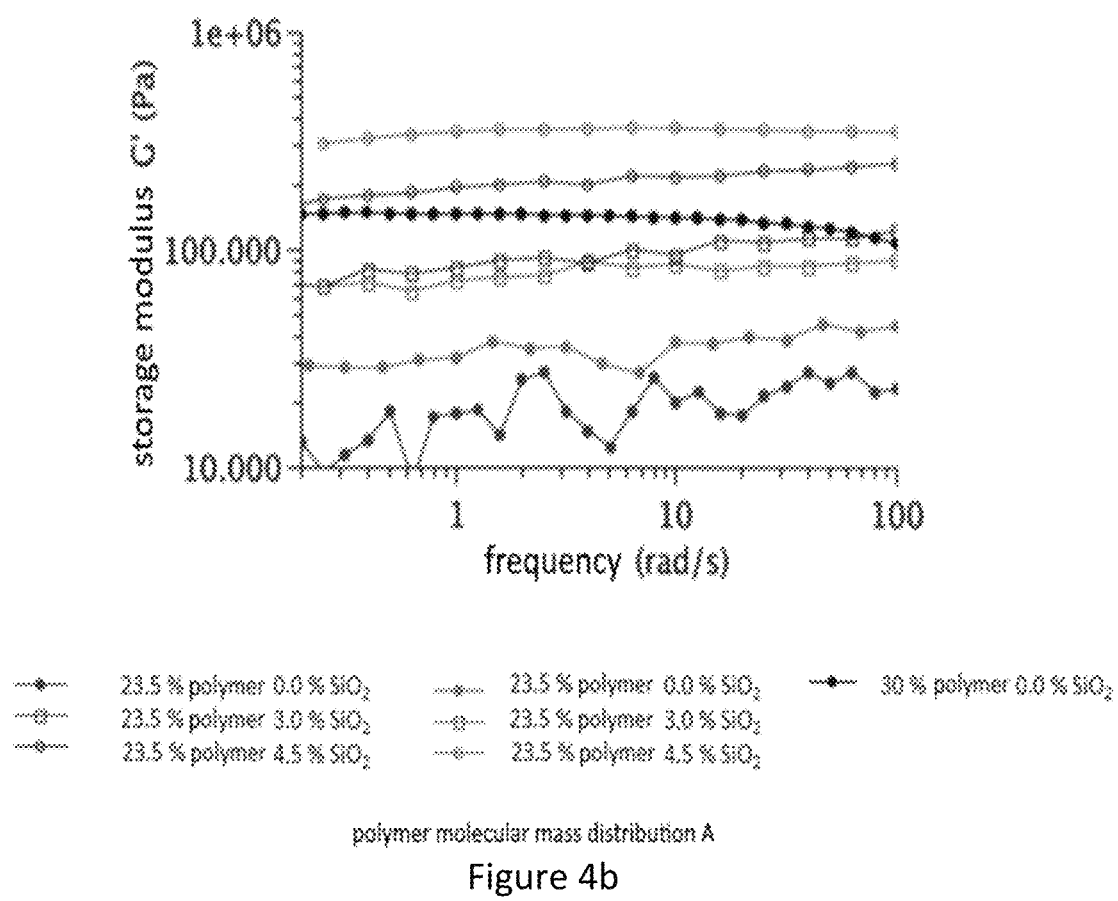
FIG. 4b shows the results of the measurement of the shear modulus as a function of frequency.

In addition, the shear modulus was measured as a function of frequency. This measurement provides information about the vibration behaviour of viscoelastic materials under oscillating shear stress and allows conclusions to be drawn about the interaction of the molecules in the system. FIG. 4b shows the storage portion of the shear modulus as a function of frequency for different hydrogels. A polymer with the molecular mass distribution A was selected here. On the one hand, the effect can be seen that the storage portion of the shear modulus increased with increasing polymer concentration. On the other hand, the storage portion of the shear modulus increased strongly with increasing $SiO_2$. For the example with 25% polymer content, the storage portion increased by 10 times if 4.5% silica nanoparticles were present in the gel. This shows the interaction between the polymer chains and the silica nanoparticles which is important for the application of the gels.

Figure 12A:
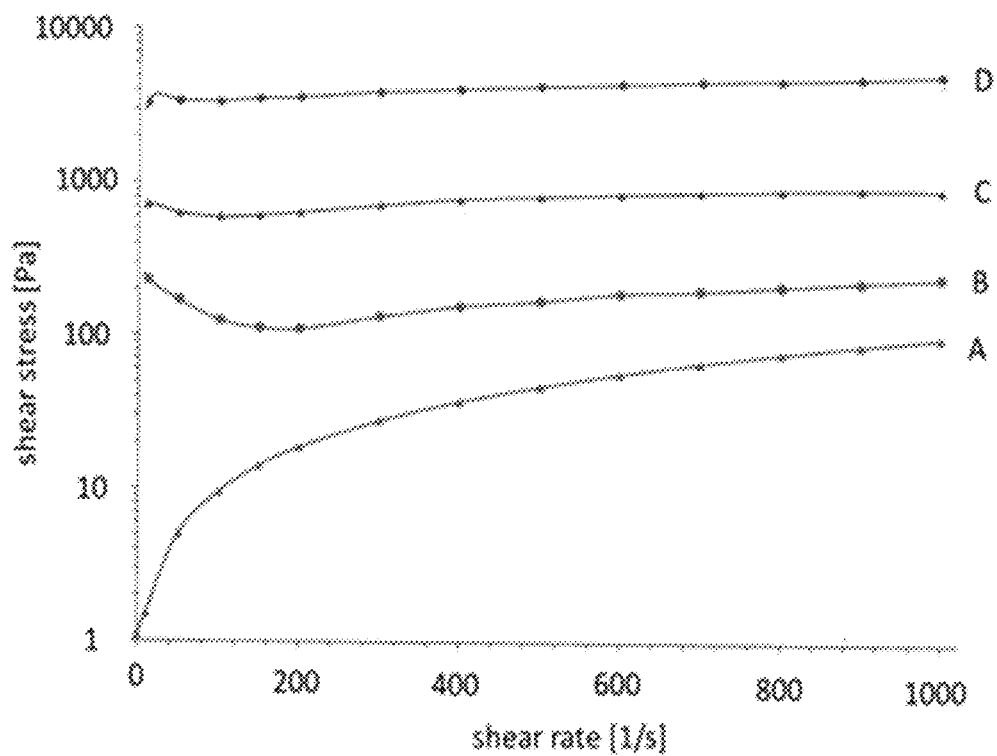
FIG. 12a shows the application of the shear ["shear stress"] as a function of the shear rate ["shear rate"] for different compositions of the carrier material: A 19.6% Kolliphor P 407, 0% $SiO_2$; B 19.6% Kolliphor P 407, 4.8% $SiO_2$; C 36.0% Kolliphor P 407, 0% $SiO_2$; D 36.0% Kolliphor P 407, 3.8% $SiO_2$.

FIG. 12a shows the shear as a function of the shear rate for different compositions of the carrier material. The shear measurements were performed at 20° C. Curve A corresponds to the carrier material with 19.6% Kolliphor without silica nanoparticles. The curve corresponds to that of a liquid, since the gel formation only begins at about 25° C. at this proportion of the Kolliphor. The curves B, C and D show a typical course for hydrogels. A flow limit is visible (shear at which the material begins to flow). Curve B shows that the addition of 4.8% $SiO_2$ converts the liquid into a gel. Curve C corresponds to the carrier material with 36.0% Kolliphor without silica nanoparticles. A gel is formed here at 20° C. by the formation of micelles. If 3.8% $SiO_2$ are added to this sample, much higher shear is required to make the material flow. Gel formation here is based on the interaction of the polymers with the silica nanoparticles.

Figure 12B:
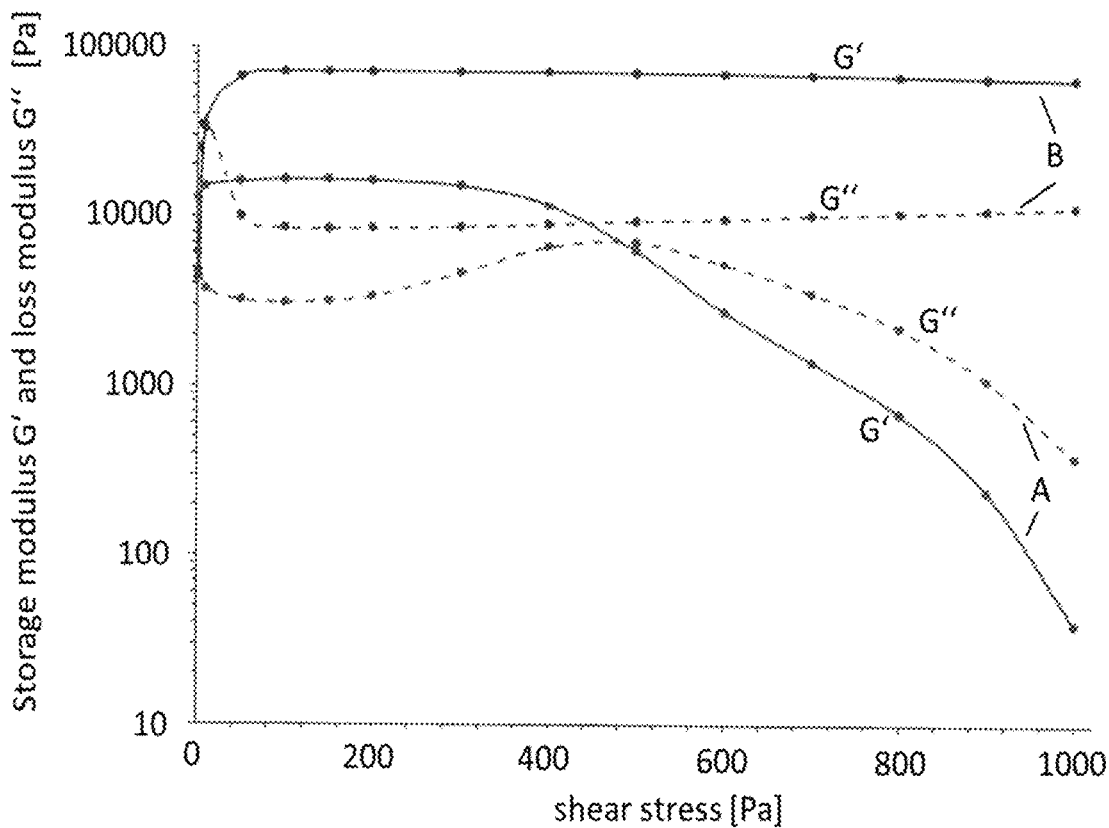
FIG. 12b shows the complex shear modulus (storage modulus ["storage modulus"] G'; loss modulus [gloss modulus"] G") for different carrier material compositions: A 36.0% Kolliphor P 407, 0% $SiO_2$; B 36.0% Kolliphor P 407, 5.0% $SiO_2$.
Figure 12C:
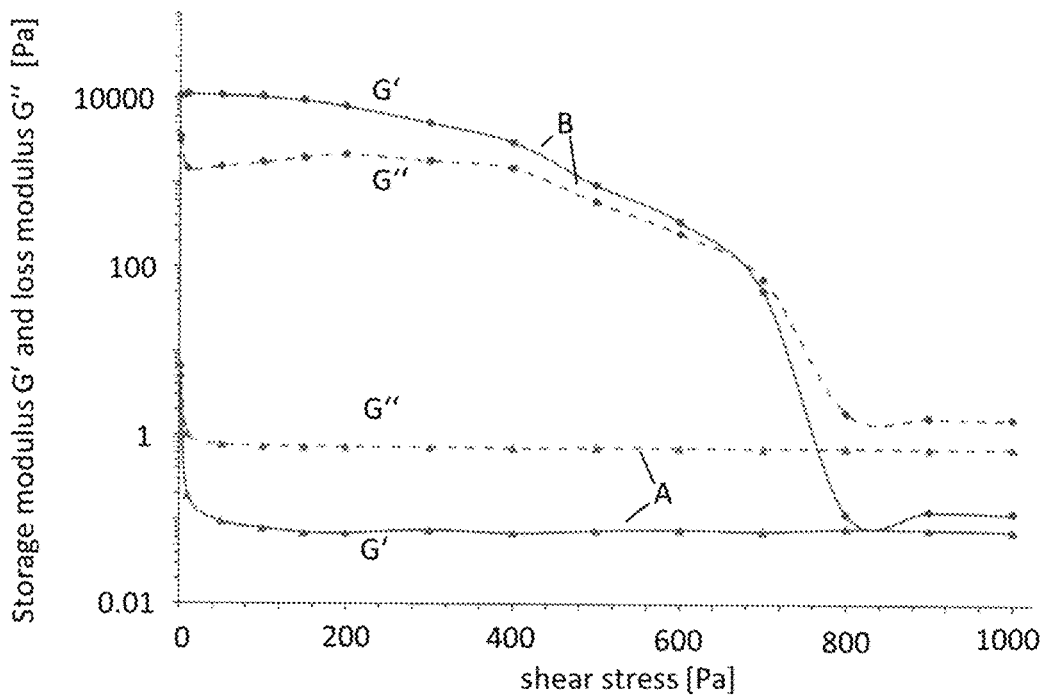
FIG. 12c shows the complex shear modulus (storage modulus G'; loss modulus G") for different carrier material compositions: A 19.4% Kolliphor P 407, 0% $SiO_2$; B 19.4% Kolliphor P 407, 4.8% $SiO_2$.
Figure 12D:
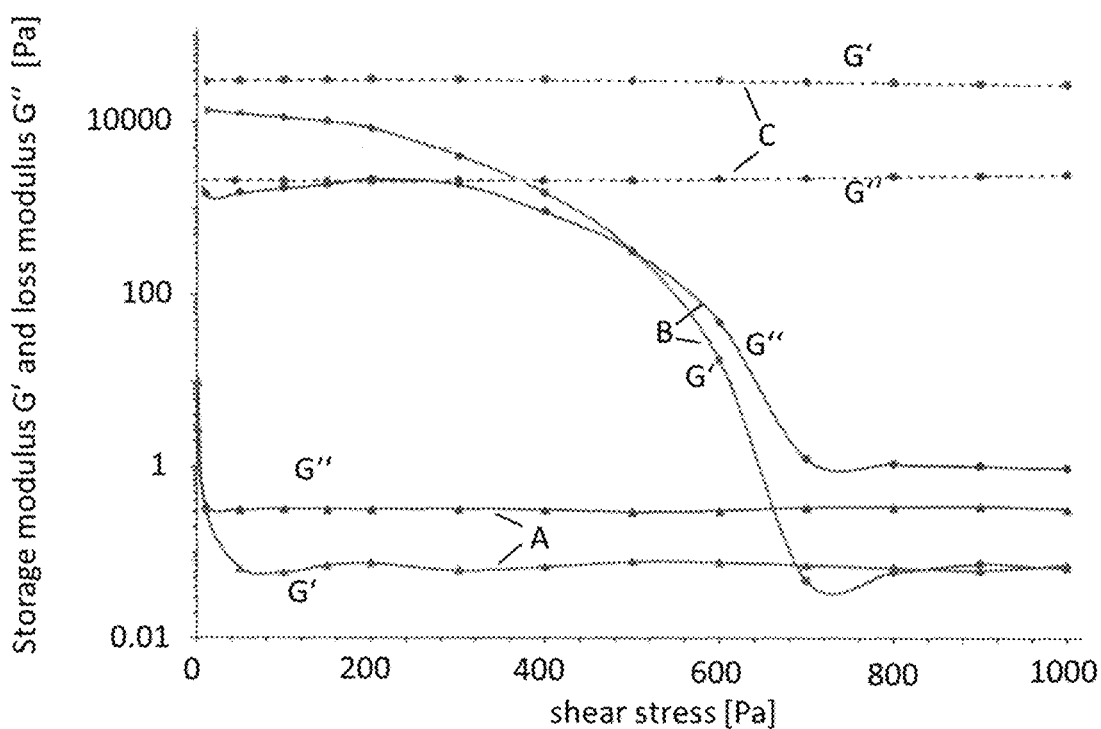
FIG. 12d shows the complex shear modulus (storage modulus G'; loss modulus G") for different carrier material compositions: A 16.4% Kolliphor P 407, 0% $SiO_2$; B 16.4% Kolliphor P 407, 5.0% $SiO_2$; C 16.4% Kolliphor P 407, 7.4% $SiO_2$.

This effect is also documented by the measurements of the complex shear modulus as a function of shear, which are shown in FIGS. 12b, 12c and 12d. The measurements were carried out at 20° C. If the storage portion G' in the curve is larger than the loss portion G", the material is a gel. If the two curves intersect, the material begins to flow. If the loss portion G" in the curve is greater than the storage portion G', the behaviour indicates a liquid.

FIG. 12b shows the behaviour of a carrier material with 36.0% Kolliphor. Without silica nanoparticles (A), the material forms a gel at 20° C. which shows transition to liquid at a shear of approx. 500 Pa. If 5% $SiO_2$ are added to the carrier material (B), the material remains a gel in the entire measuring range. The curves of G' and G" hardly approach each other. For the application this means that the carrier material with silica nanoparticles is much more stable and ensures improved handling.

FIG. 12c shows this effect for smaller Kolliphor concentrations (19.6%). Without silica nanoparticles there is no gel formation at 20° C. However, the addition of silica nanoparticles leads to gel formation. FIG. 12c documents the dependence of this effect on the $SiO_2$ concentration. The starting point is a carrier material with 16.4% Kolliphor, which does not form a gel at 20° C. (A). By adding 5.0% $SiO_2$, the material becomes a gel which shows transition to liquid at a shear rate of approx. 500 Pa (B). With 7% $SiO_2$ a gel is formed which proves to be stable in the entire measuring range (C). These results show that the rheological properties of the composition can be modulated by changing the ratio of Kolliphor, silica nanoparticles and water. This makes it possible to optimize the carrier material specifically for different applications.

Example 2: Embedding of Porous Bone Substitute Materials

Osteoinductive granules of hydroxyapatite (HA) in the form of fir cones were used (Nanobone, Artoss GmbH, Rostock, Germany). These were on average 3 mm long and had a diameter between 0.5 and 1.0 mm. The HA showed a crystallographic morphology similar to that of biological HA. This HA was embedded in a highly porous matrix of silica xerogel. The porosity of the granules was about 50%, the specific surface area was about 200 m$^2$/g, and the pore size distribution showed a maximum at 4 nm.

The granules were impregnated in a mass ratio of 1:1 with a pure silica sol with a SiO$_2$ concentration of 6% and a pH value of 7.0. In contact with the solid, the silica sol gels. Granules are produced which are filled with a silica gel and are coated with same.

Figure 6:
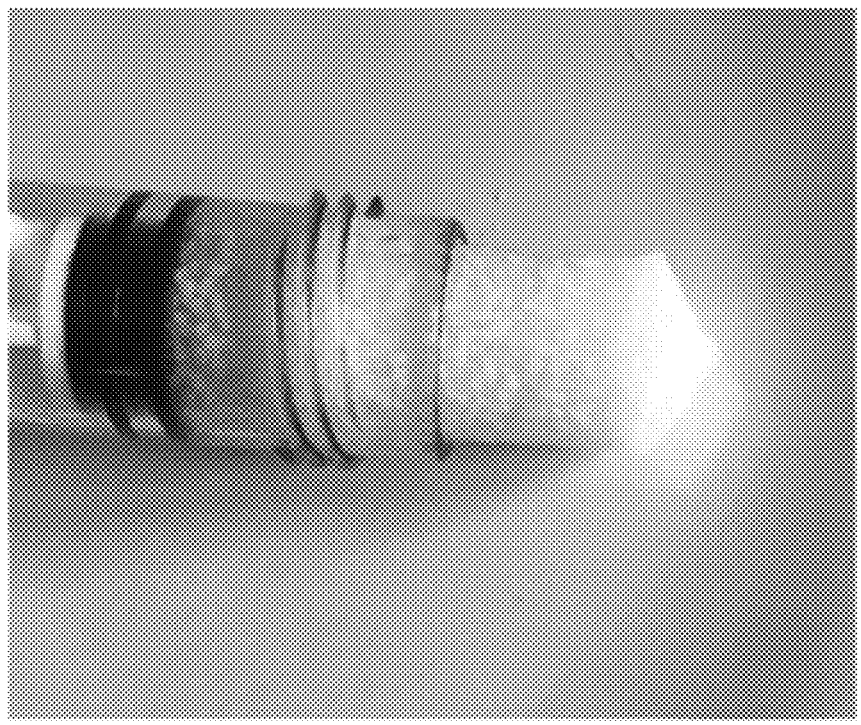
FIG. 6 shows the application of the bone substitute material of the invention with an applicator.

To produce the poloxamer-silica hydrogel, 35 g Kolliphor P 407 (BASF) were stirred in 65 g silica sol with a SiO$_2$ content of 6%. The sol was previously cooled to 1° C. Cross-linking is achieved by gamma irradiation in the range of 17.5 to 30 kGrey. This polymer-silica hydrogel was mixed with the coated granules in a mass ratio of 1:1. The resulting pasty bone substitute material is very easy to shape and can be inserted into bone defects with an applicator. FIG. 6 shows the use of the bone substitute material with an applicator.

Figure 7:
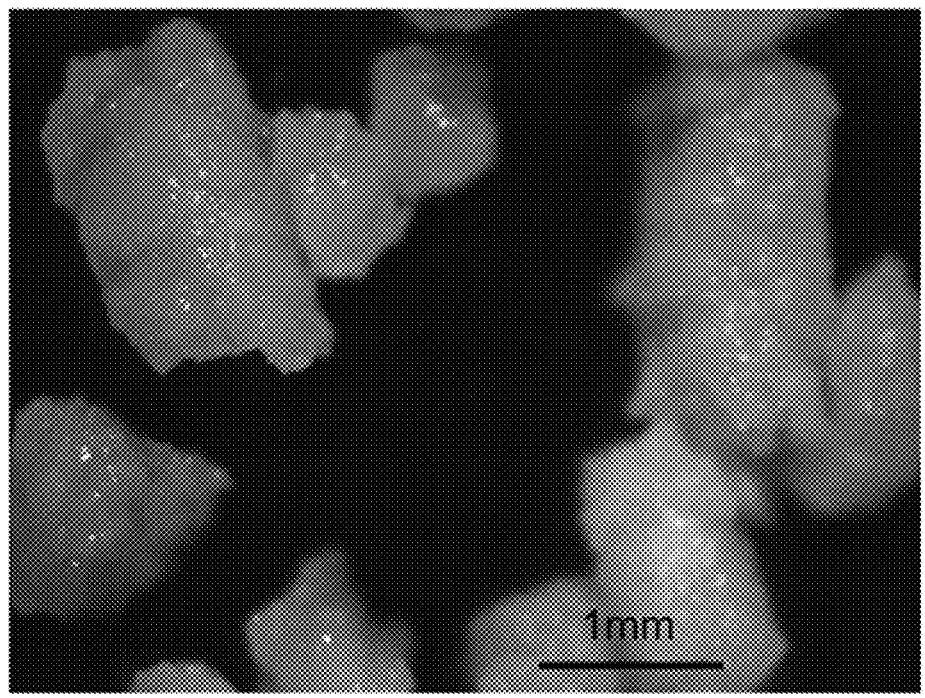
FIG. 7 shows the result of an examination of the bone substitute material of the invention after accelerated aging by means of reflected light microscopy.

The stability of the coating of the granules with pure silica hydrogel was controlled by subjecting the material to accelerated ageing for 1 year according to ASTM F 1980-07. After removing the poloxamer-silica hydrogel by rinsing with water, granules coated with pure silica hydrogel could be seen under the microscope. FIG. 7 shows the analysis of the granules using reflected light microscopy.

Example 3: Functionality in Animal Experiments

The experiments were carried out with female rabbits (New Zealand White, 3-4 kg, Charles River, Sulzfeld, Germany). The bone substitute material produced according to Example 2 was implanted bilaterally into the hind legs. The cut through the cutis and subcutis has a length of approx. 2.5 cm. The musculature was also severed in a small area in order to keep the injuries as small as possible, and then the periosteum was carefully detached from the bone at the defect site to be placed. A cylindrical defect (5 mm in diameter and 10 mm in length) was then inserted into each of the lateral condyles of the femora. A standard drill (Ø 4.5 mm) was used for this purpose. During defect settlement, the area was rinsed with 0.9% NaCl solution to prevent necrosis of bone tissue due to heat exposure.

Anaesthesia was administered subcutaneously to the neck fold by injection of 10% ketamine (30-60 mg/kg body weight) and 2% xylazine (5 mg/kg body weight). After 10 min, 0.3 ml atropine (0.5 mg/ml) was administered. In addition, novamine sulfone (500 mg/ml) was injected as an analgesic and penicillin G (intramuscular 150,000 i.U.) as an antibiotic. Local anaesthesia was performed with 2 ml xylocitin-loc (2%/ml). After implantation, the wound area was rinsed with gentamicin (80 mg/2 ml, 1:5 dilution with NaCl). The wound closure (point seam) was made with vicryl suture material.

After trial periods of 4, 8 and 12 weeks, the corresponding trial groups were removed from the trial. The euthanasia was performed on the anaesthetised animal (10% ketamine and 2% xylazine, subcutaneously) using Release® (300 mg/ml corresponding to: 1 ml/kg body weight) intravenously. Histological sections were made for the evaluation. The defect regions were explanted, decalcified and embedded in paraffin. A hematoxylin and eosin stain was applied.

Figure 8:
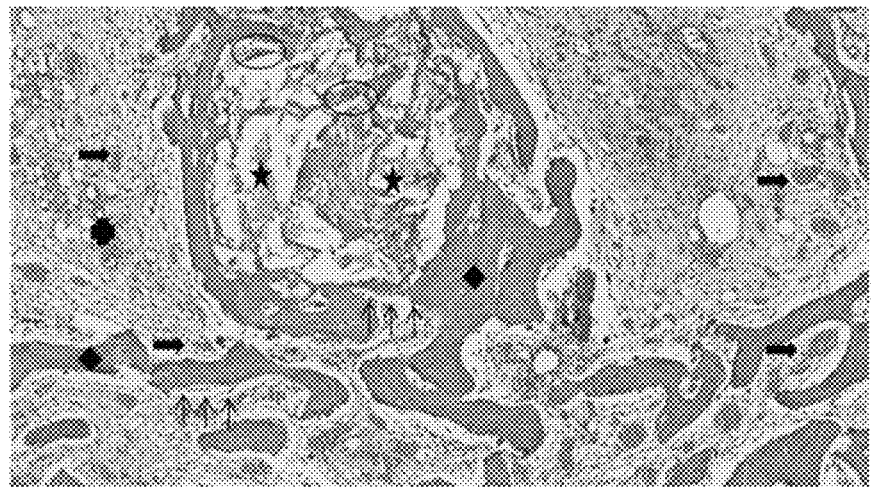
FIG. 8 shows the result of a HE staining 4 weeks after implantation of the bone substitute material of the invention into the hind leg of a rabbit.
Figure 9:
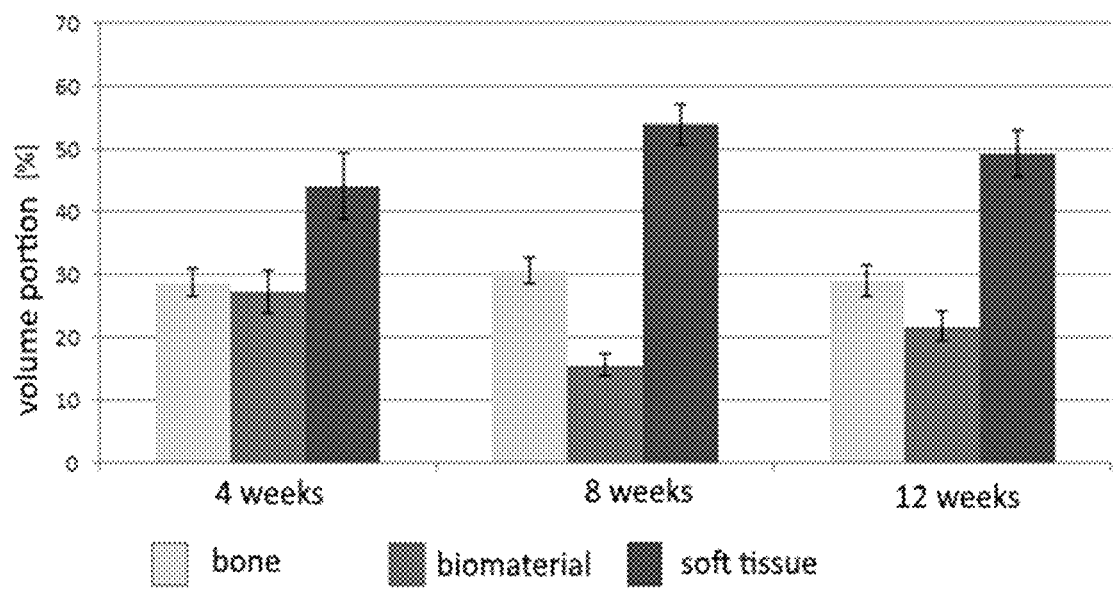
FIG. 9 shows the result of one of the histomorphometric evaluation after implantation of the bone substitute material of the invention into the hind leg of a rabbit.
Figure 10:
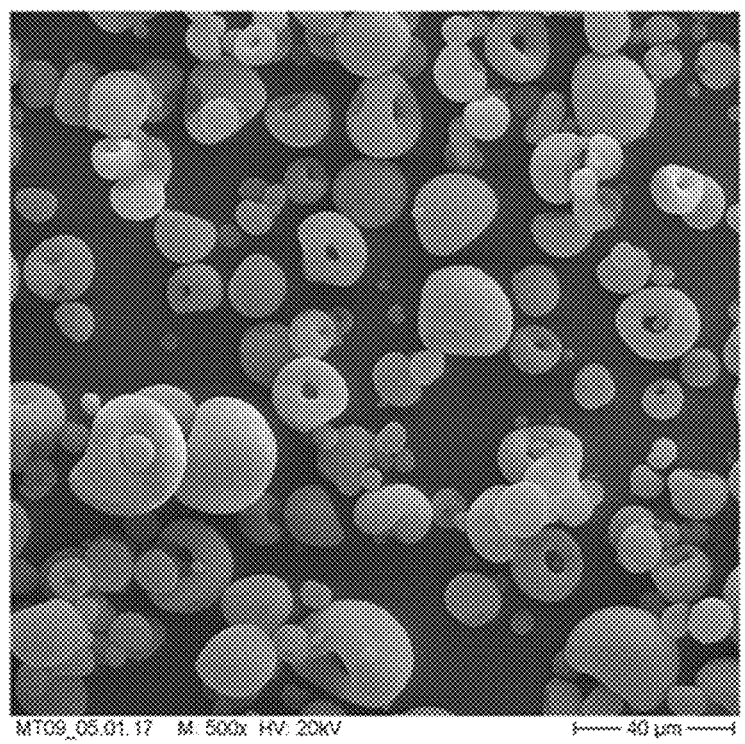
FIG. 10 shows the use of microparticles in the form of hollow spheres with an opening and a diameter of about 40 µm in the bone substitute material of the invention.
Figure 11:
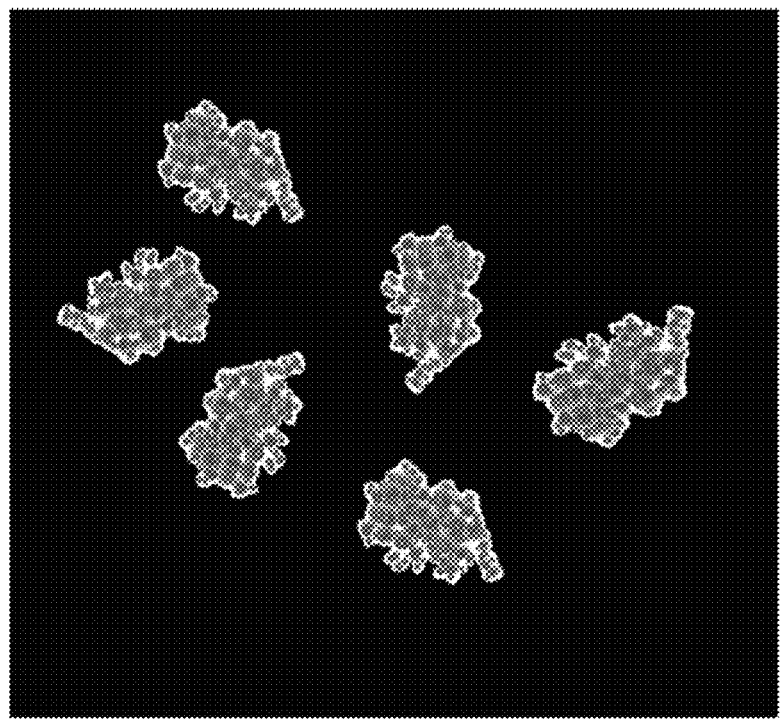
FIG. 11 schematically shows the coating of clusters of microparticles with pure silica hydrogel before embedding them in the poloxamer-silica hydrogel.

Result: After 4 weeks neither the polymer-silica hydrogel nor the pure silica hydrogel was detectable. A complete resorption occurred. Changes in the temporal sequence to granules embedded in the patient's blood were not detectable during defect healing. FIG. 8 shows a histological image (HE staining) 4 weeks after the procedure. New bone formation and resorption of the granules is not influenced by the original embedding in the two hydrogels. The results of the histomorphometric evaluation of the animal experiments are shown in FIG. 9. A defect healing is documented.

The invention claimed is:

1. A carrier composition for particulate and granular bone substitute materials, wherein the carrier composition is a hydrogel comprising:
    (a) an ethylene oxide (EO)-propylene oxide (PO) block copolymer or a mixture of ethylene oxide (EO)-propylene oxide (PO) block copolymers; and
    (b) silica nanoparticles with a size of between about 0.5 nm and about 10 nm.

2. The carrier composition according to claim 1, wherein the proportion of water in the hydrogel ranges from 60% to 90%.

3. The carrier composition according to claim 1, wherein the proportion of ethylene oxide (EO)-propylene oxide (PO) block copolymers in the hydrogel is between about 10% and 40% (w/w).

4. A carrier composition according to claim 1, wherein the proportion of silica nanoparticles is between about 2% and 12% (w/w).

5. A carrier composition according to claim 1, wherein the silica nanoparticles have a size between about 0.5 nm and 1.5 nm.

6. A carrier composition according to claim 1, wherein the silica nanoparticles form fractal aggregation clusters having an average size of less than 200 nm.

7. A carrier composition according to claim 1, wherein the ethylene oxide (EO)-propylene oxide (PO) block copolymers in the carrier composition have a molecular weight distribution between about 1,000 g/mol and 70,000 g/mol.

8. A carrier composition according to claim 1, wherein at least 30% (w/w) of the ethylene oxide (EO)-propylene oxide (PO) block copolymers in the carrier composition consist of a poloxamer.

9. A bone substitute material comprising:
    (a) a carrier composition according to claim 1; and
    (b) osteoconductive and/or osteoinductive particles or osteoconductive and/or osteoinductive granules.

10. A bone substitute material according to claim 9, wherein the osteoconductive or osteoinductive particles have a size between about 5 μm and 100 μm.

11. A bone substitute material according to claim 9, wherein the osteoconductive or osteoinductive particles are hollow spheres having an opening.

12. A bone substitute material according to claim 11, wherein the hollow spheres form clusters of a size between about 100 μm and 3,000 μm.

13. A bone substitute material according to claim 9, wherein the osteoconductive or osteoinductive particles or the osteoconductive and/or osteoinductive granules consist of hydroxyapatite crystallites which have the morphology of the biological hydroxyapatite of the bone and are coated with a matrix of silica xerogel.

14. A bone substitute material according to claim 9, wherein the osteoconductive and/or osteoinductive particles or the osteoconductive and/or osteoinductive granules are coated with a silica gel.

15. A process for the preparation of a bone substitute material comprising the steps of
    (a) providing a carrier composition according to claim 1;
    (b) optionally treating the carrier composition with gamma radiation; and
    (c) mixing the carrier composition with osteoconductive and/or osteoinductive particles or with osteoconductive and/or osteoinductive granules.

16. A carrier composition according to claim 8, wherein said poloxamer is poloxamer 407.

17. A carrier composition according to claim 8, wherein said poloxamer has an average molecular weight in the range of 9,800 to 14,600 g/mol.

18. A bone substitute material according to claim 14, wherein the silica concentration in the silica gel is between about 3% and 10%.

19. The process of claim 15, wherein the osteoconductive and/or osteoinductive particles or the osteoconductive and/or osteoinductive granules are coated with a silica hydrogel.

* * * * *